(12) United States Patent
Zamierowski et al.

(10) Patent No.: US 7,662,112 B2
(45) Date of Patent: Feb. 16, 2010

(54) MEDICAL MEASURING DEVICE AND METHOD

(75) Inventors: David S. Zamierowski, Overland Park, KS (US); Robin S. Hursh, Lenexa, KS (US)

(73) Assignee: KCI Licensing, Inc., San Antonio, TX (US)

( * ) Notice: Subject to any disclaimer, the term of this patent is extended or adjusted under 35 U.S.C. 154(b) by 409 days.

(21) Appl. No.: 11/129,614

(22) Filed: May 13, 2005

(65) Prior Publication Data

US 2006/0258961 A1    Nov. 16, 2006

(51) Int. Cl.
*A61B 5/103* (2006.01)
(52) U.S. Cl. ..................................... 600/587
(58) Field of Classification Search .............. 600/300, 600/587, 407, 409; 382/128; 604/24, 290
See application file for complete search history.

(56) References Cited

U.S. PATENT DOCUMENTS

| 5,807,280 | A | | 9/1998 | Davis |
| 5,860,923 | A | * | 1/1999 | Lenker et al. ............... 600/433 |
| 6,159,167 | A | * | 12/2000 | Hardin-Naser .............. 600/587 |
| D440,659 | S | | 4/2001 | Ogino et al. |
| 6,381,488 | B1 | | 4/2002 | Dickey et al. |
| 6,413,212 | B1 | * | 7/2002 | Raab .......................... 600/300 |
| 6,454,720 | B1 | | 9/2002 | Clerc et al. |
| 6,640,460 | B1 | * | 11/2003 | Nabarro et al. ................ 33/759 |

FOREIGN PATENT DOCUMENTS

| JP | 2004-073769 | 3/2004 |
| JP | 2004-073769 | 11/2004 |

OTHER PUBLICATIONS

Kosaka, M. et al.: "Pocket Measure: An Exclusive Tool for Measuring and Recording Pressure Ulcer Pockets", Plastic and Reconstructive Surgery, Aug. 2004, pp. 624-625, vol. 114, No. 2, American Society of Plastic Surgeons.
Masaaki Kosaka, M.D., et al.; "Pocket Measure": An Exclusive tool for Measuring and Recording Pressure Ulcer Pockets; Plastic and Reconstructive Surgery, Aug. 2004, vol. 114, No. 2, p. 624-625; U.S.A.
US Marketing Services Worldwide Web Site (www.usmsinc.com); advertising for the "Wound Stick Measuring Stick", "Wound Stick Tunneler" and "Wound Map" products.

* cited by examiner

*Primary Examiner*—Max Hindenburg
*Assistant Examiner*—Fangemonique Smith

(57) ABSTRACT

A subsurface wound measuring device and method are provided for measuring a subsurface wound or cavity of a patient, the device including a flexible strip having first and second sections, the sections having first and second ends respectively with an intermediate bend being located between the first and second ends. The first end is adapted for being located internally to a patient, the second end being adapted for being located externally to the patient. The first and second sections have generally concave-shaped cross-sections with measuring indicia being located along at least one of the sections. The device also optionally includes a measuring strip and a receiver mounted on the second end for receiving the measuring strip, where the measuring strip and the flexible strip form complementary structure for measuring a subsurface wound or cavity.

2 Claims, 9 Drawing Sheets

FIG. 4

MEDICAL MEASURING DEVICE AND METHOD

BACKGROUND OF THE INVENTION

1. Field of the Invention

The present invention relates generally to medical measuring devices and methods, and in particular to wound modeling and treatment applications of same.

2. Description of the Related Art

In the medical field, wound treatment encompasses a wide variety of procedures, pharmacologicals, devices and equipment. Health care institutions and other providers commonly devote substantial resources to wound treatment. Treating open wounds, such as those associated with decubitus pressure ulcers and other chronic conditions, can be particularly challenging. For example, wound care facilities commonly specialize in the treatment of open, slow-healing wounds.

Certain types of open wounds exhibit subdermal voids and pockets whereby intact skin areas are undermined by infected and necrotic tissue. Such subdermal conditions can be difficult to treat because they are not readily observable and do not respond to surface-applied treatment protocols. For example, an undermined wound may appear to be closing at the epidermis, when in fact subdermal conditions are actually worsening. Determining the extent of subsurface wounds is an important aspect of monitoring treatment progress and selecting appropriate treatment protocols.

The related art includes devices and procedures for measuring and modeling open and subsurface wounds. For example, US Marketing Services Worldwide (USMS) of Miami, Florida offers a Wound Stick™ Measuring System with calibrated rulers adapted for measuring open wounds and a Wound Stick Tunneler™ for insertion into undermined pressure wounds. The measurements can be used to produce a WoundMap™ record, which documents the extent of subsurface injury. Another related art device is shown in Japanese Patent Abstract Publication No. 2004-073,769, which discloses a decubitus pocket measure including a probe and a measure, which enable marking the skin surface above the undermined portion of the wound. The use of this device is described in Kosaka, M. et al., "Pocket Measure": an Exclusive Tool for Measuring and Recording Pressure Ulcer Pockets, *Journal of Plastic and Reconstructive Surgery*, August 2004, pp. 644-25.

A wound measuring device for open and subsurface wounds would ideally be adapted for obtaining multiple measurements of irregular shapes, such as undermined wounds, and using such measurements for generating two-dimensional or three-dimensional models. Patient comfort and use of operation are additional considerations. The present invention addresses these considerations. Heretofore there has not been available a medical measuring device and method with the advantages and features of the present invention.

SUMMARY OF THE INVENTION

In the practice of one aspect of the present invention, a wound measurement device is provided, which includes a flexible strip adapted for bending at an elbow whereby first and second sections with respective first and second ends are formed. The strip includes an upper surface with a measuring structure and a configuration adapted for inserting, guiding and manipulating same within a wound. Alternative embodiment measuring devices include different end constructions, guide and measuring strips adapted for cooperative, sliding engagement, and other optional features. In the practice of one aspect of the method of the present invention, multiple dimensions corresponding to the size and shape of the wound are determined whereby it can be modeled in two or three dimensions. The method can include monitoring the patient's progressive healing and response to treatment.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, up, down, front, back, right and left refer to the invention as oriented in the view being referred to. The words "inwardly" and "outwardly" refer to directions toward and away from, respectively, the geometric center of the embodiment being described and designated parts thereof. Forwardly and rearwardly are generally in reference to the direction of travel, if appropriate. Said terminology will include the words specifically mentioned, derivatives thereof and words of similar meaning.

II. Wound Measuring Device 2

Figures 1, 2:
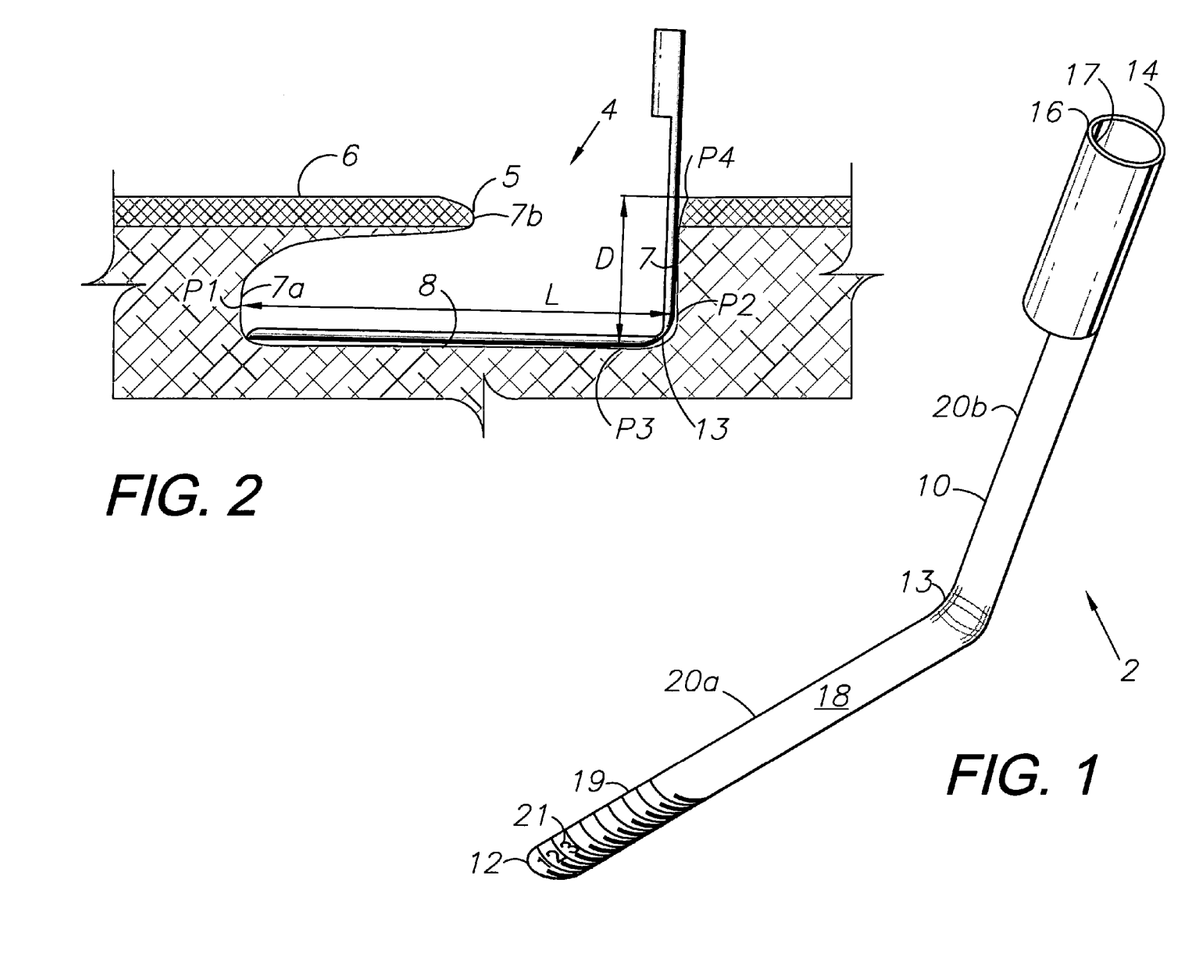
FIG. 1 is a perspective view of a subsurface wound measuring device embodying the present invention.
FIG. 2 is a cross-section of a wound, with the measuring device partly inserted therein.

Referring to the drawings in more detail, the reference numeral 2 generally designates a subsurface wound measuring device embodying the present invention. Without limitation on the generality of useful applications of the device 2, as shown in FIG. 2, it is particularly useful for obtaining linear dimensions corresponding to the size and configuration of an undermined subsurface wound cavity 4, which includes an opening 5 at the skin layer 6, a sidewall 7 with an inner portion 7a adjacent to a wound base 8 an outer portion 7b adjacent to the opening 5. The sidewall inner portion 7a is larger than the outer portion 7b, whereby the wound cavity 4 undermines the patient's skin layer 6. Such an undermined configuration presents difficulties in directly obtaining measurements since the sidewall inner portion 7a is largely obscured. The wound cavity 4 can extend to the fascia layer and beyond. The measuring device 2 is adapted for taking multiple linear measurements of a wound, not only of the skin opening but also of the irregular configuration of the undermined portion, including lengths, widths and depths. Such measurements can be used to generate a model of the wound in two or three dimensions.

The measuring device 2 generally includes a flexible, upwardly-concave strip 10 with first and second ends 12, 14. The first end 12 can be radiused as shown for patient comfort. The concavity of the strip 10 facilitates bending at an elbow 13 whereby first and second sections 20a, 20b are formed adjacent to the ends 12, 14 respectively. The respective lengths of the sections 20a, 20b can vary along the length of the strip 10, depending upon where the elbow 13 is formed. A tubular sleeve 16 is mounted on the strip 10 adjacent to its second end 14, and includes a sleeve passage 17. The sleeve 16 is adapted for grasping, e.g. with the thumb and forefinger, whereby the device 2 can be positioned, guided and manipulated within the wound cavity 4.

The strip 10 includes an upper surface 18, which can be provided with measuring structure comprising a printed scale 19 corresponding to suitable linear values represented by indicia 21, such as centimeters. The scale 19 can extend for the length of the strip 10 and can originate at the first end 12.

Figure 3A:
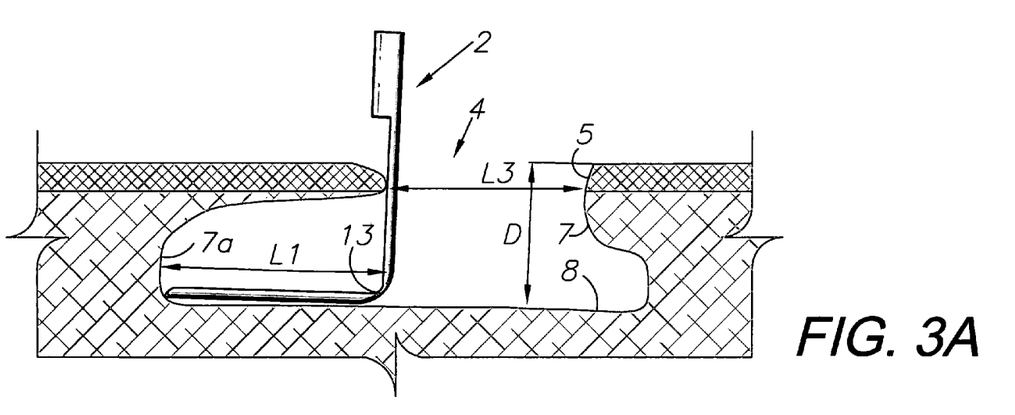
FIG. 3A is a cross-section of another wound, with the measuring device partly inserted therein.
Figure 3B:
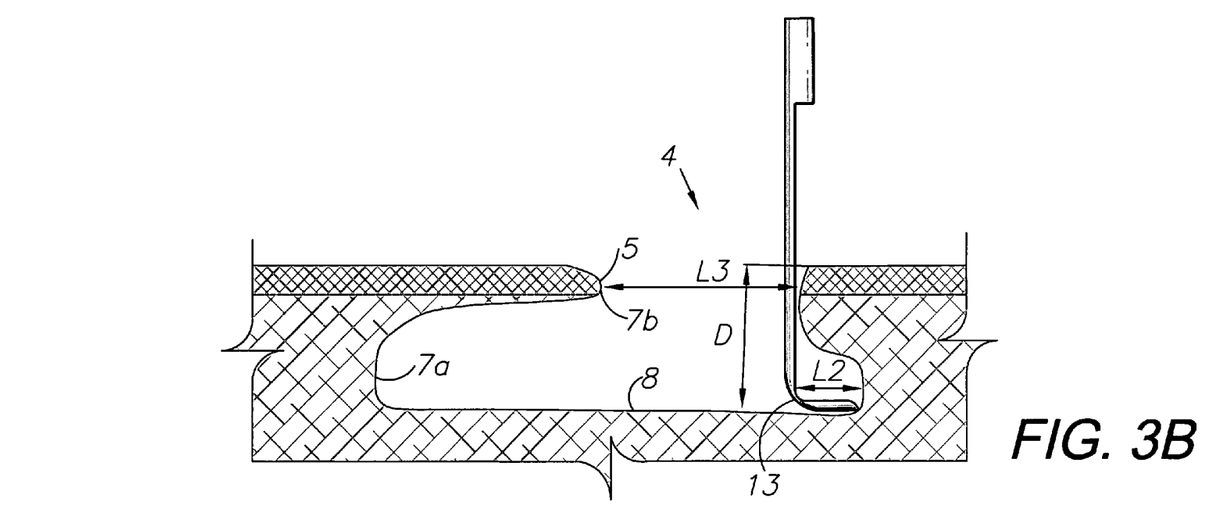
FIG. 3B is another cross-section of the wound shown in FIG. 3A, showing additional measurements being taken with the measuring device partly inserted in another orientation.

FIG. 2 shows the device 2 placed in the wound cavity 4 for measuring same according to the method of the present invention. An elbow 13 can be formed with the strip first section 20a extending generally horizontally therefrom to a first point P1 at its first end 12 on the cavity sidewall inner portion 7a. A first distance L1 from the elbow 13 to P1 can be measured, observed and recorded. The depth D, as measured from point P3 to P4 can be determined with the measuring device 2 (FIG. 2). It will be appreciated a number of measurements can be taken, as appropriate for the nature of the wound, the precision requirements for measuring same, etc. FIGS. 3A and 3B show the measuring device 2 being used to obtain measurements of the wound 4 in a different area thereof. For example, the undermined, wound inner portion 7a can extend in multiple directions from the wound opening 5. Thus, a first length measurement is taken to determine L1 in a first undermined area, a second length measurement determines L2 in a second undermined area and the third length measurement L3 is taken across the opening 5. The overall length of the wound 4 is thus the sum of L1+L2+L3. The depth D of the wound 4 can also be determined as shown. Additional measurements can be taken as needed, for example to determine distances between various opposite points on the wound sidewall. Given the generally irregular configurations of wounds, which configurations change with healing, it will be appreciated that multiple dimensional values may be required in order to accurately model a wound in two or three dimensions and monitor its healing progress.

III. Alternative Embodiment Wound Measuring Devices

Figure 4:
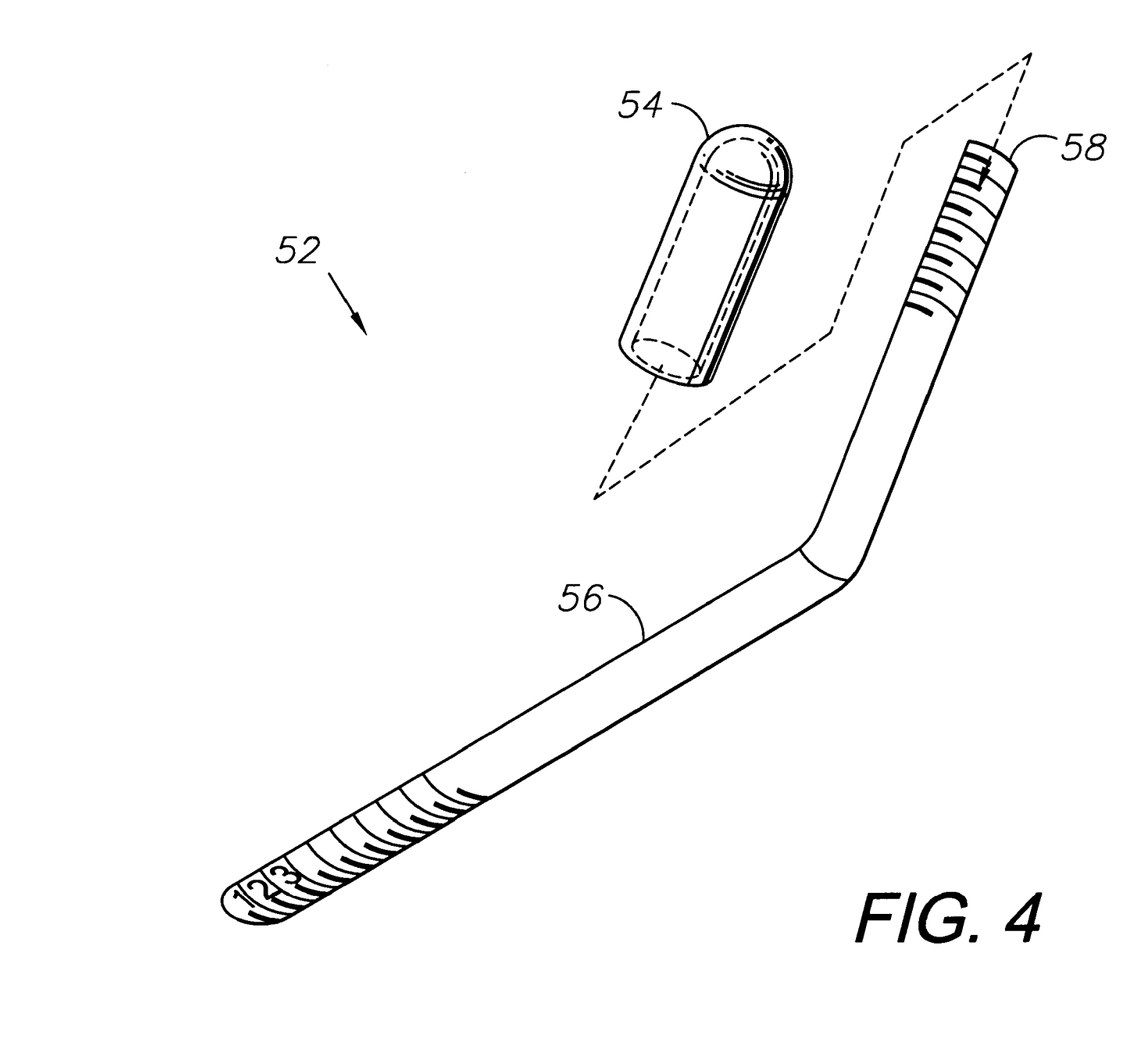
FIG. 4 is a perspective view of a subsurface wound measuring device comprising an alternative embodiment of the present invention.
Figures 5, 7:
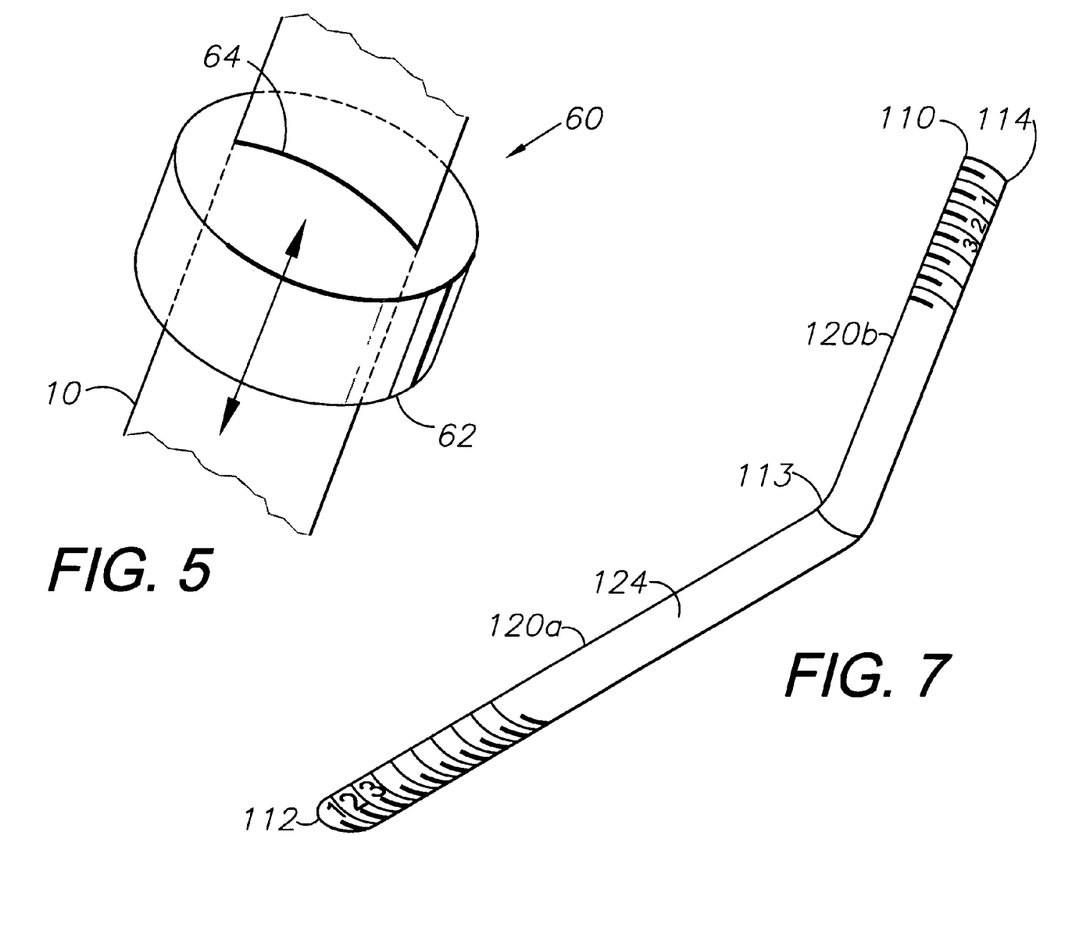
FIG. 5 is a fragmentary, perspective view of a subsurface wound measuring device comprising another alternative embodiment of the present invention.
FIG. 7 is a perspective view of a measuring strip thereof.

FIG. 4 shows a measuring device 52 comprising an alternative embodiment of the present invention. The device 52 includes a removable tip 54 adapted for mounting on a strip 56 second end 58 to facilitate gripping, guiding, inserting and manipulating same. FIG. 5 shows another alternative embodiment measuring device 60 of the invention with a collar 62 including an arcuate slot 64 slidably receiving the strip 10 or the strip 56 and adapted for gripping to facilitate inserting, positioning and guiding the strip 10 or 56.

Figures 6A, 6B:
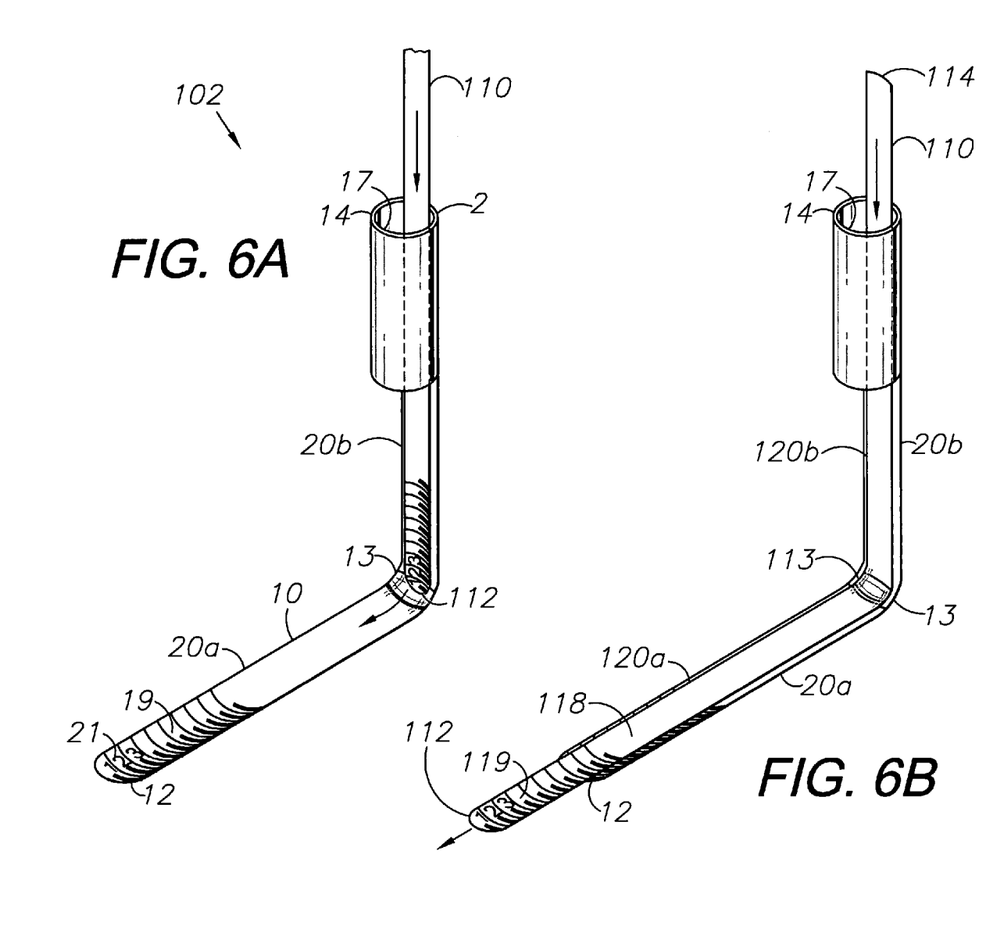
FIGS. 6A and 6B are perspective views of a subsurface wound measuring device comprising an alternative embodiment of the present invention.

FIGS. 6A, 6B and 7 show another alternative embodiment wound measuring device 102, including a measuring strip 110 with first and second ends 112, 114 associated with respective first and second sections 120a, 120b separated by an elbow 113. The measuring strip 110 has an arcuate, upwardly-concave configuration with an upper surface 118 including a measuring structure comprising a scale 119. The measuring strip 110 is adapted for use in conjunction with the measuring device 2 described above, which in this configuration provides a guide strip 10 for guiding and directing the measuring strip 110 into and within the wound cavity 4. As shown in FIGS. 6A and 6B, the sleeve passage 17 telescopically and slidably receives the measuring strip 110, which forms an elbow 113 adjacent to the elbow 13 whereby the measuring strip sections 120a, 120b partly overlie the respective guide strip sections 20a, 20b. The measuring strip 110 can thus be advanced into the wound cavity 4 and extended to engage its sidewalls 7a, 7b, with the guide strip 10 providing a layer of protection and between the measuring strip 110 and the patient, particularly along the wound base 8. FIG. 7 shows the measuring strip 110 separated from the guide strip 10. It will be appreciated that the guide and measuring strips 10 and 110 (FIGS. 1 and 7 respectively) can be used together in the measuring device 102 configuration described above or independently.

Figures 8, 9:
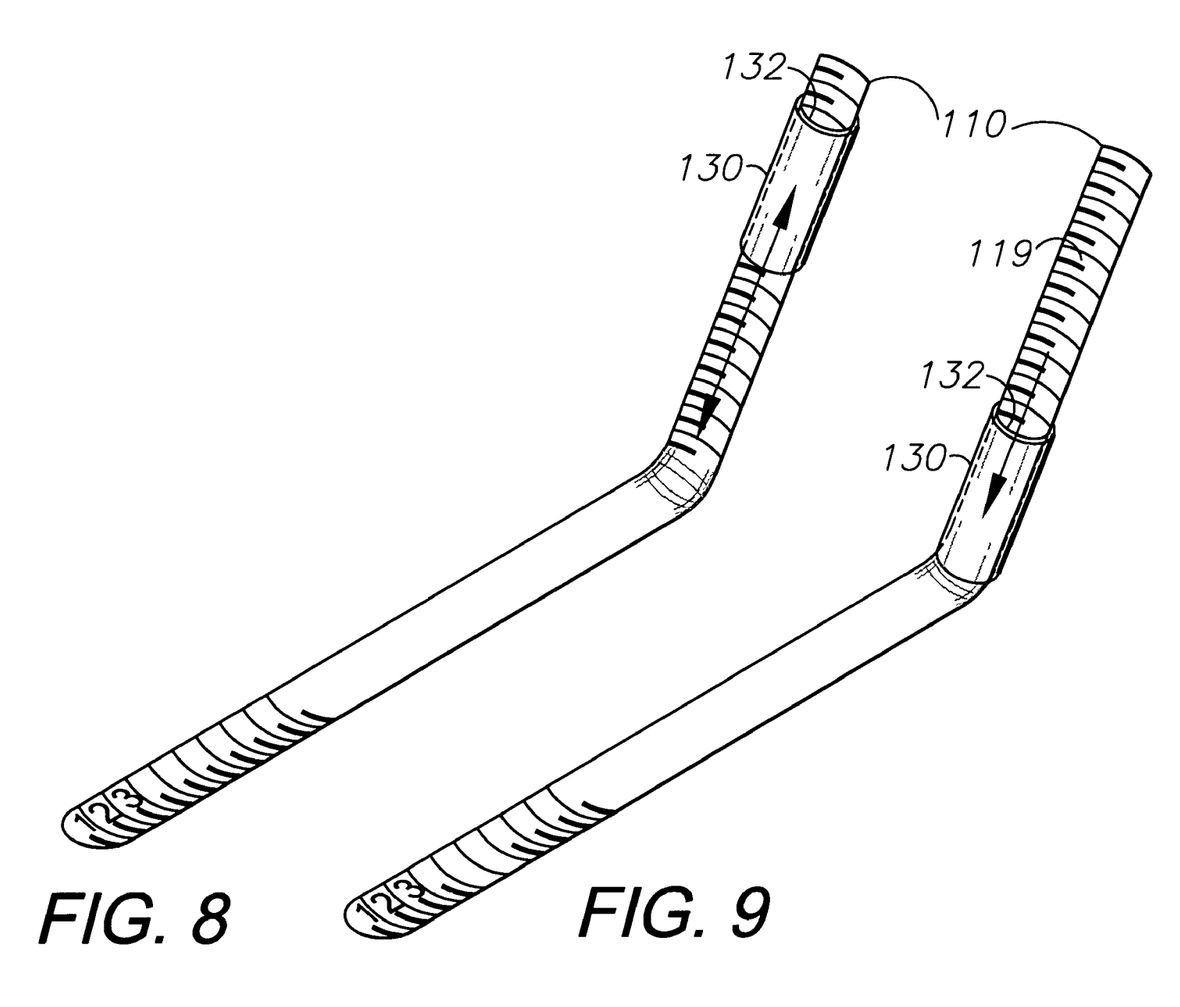
FIGS. 8 and 9 are perspective views of a subsurface wound measuring device comprising another alternative embodiment of the present invention.

FIGS. 8 and 9 show the measuring strip 110 fitted with a movable sleeve 130 having a passage 132, which telescopically and slidably receives the measuring strip 110. The movable sleeve 130 is adapted for providing an index whereby a location along the length scale 119 can be marked for reference, e.g. when the measuring strip 110 is extracted. The strip 10 can also be fitted with the movable sleeve 130 for indexing particular locations along its length.

The measuring strip 110 can be placed on the guide strip 10 of the measuring device 2, and held digitally in place to mark a spot (e.g. the elbow 13 position) for a measurement, which can be readily read when the guide and measuring strips 10, 110 are extracted together from the wound cavity 4. Alternatively, any relatively stiff, sterile available material, such as a cotton-tipped applicator, can be used with the guide strip 10 to obtain a measurement. The sleeve 130 shown in FIGS. 8 and 9 can be freely movable and also require external fixation to hold and mark a position, or it can have an internal fixing and releasing device or spring.

Figures 10, 11, 12:
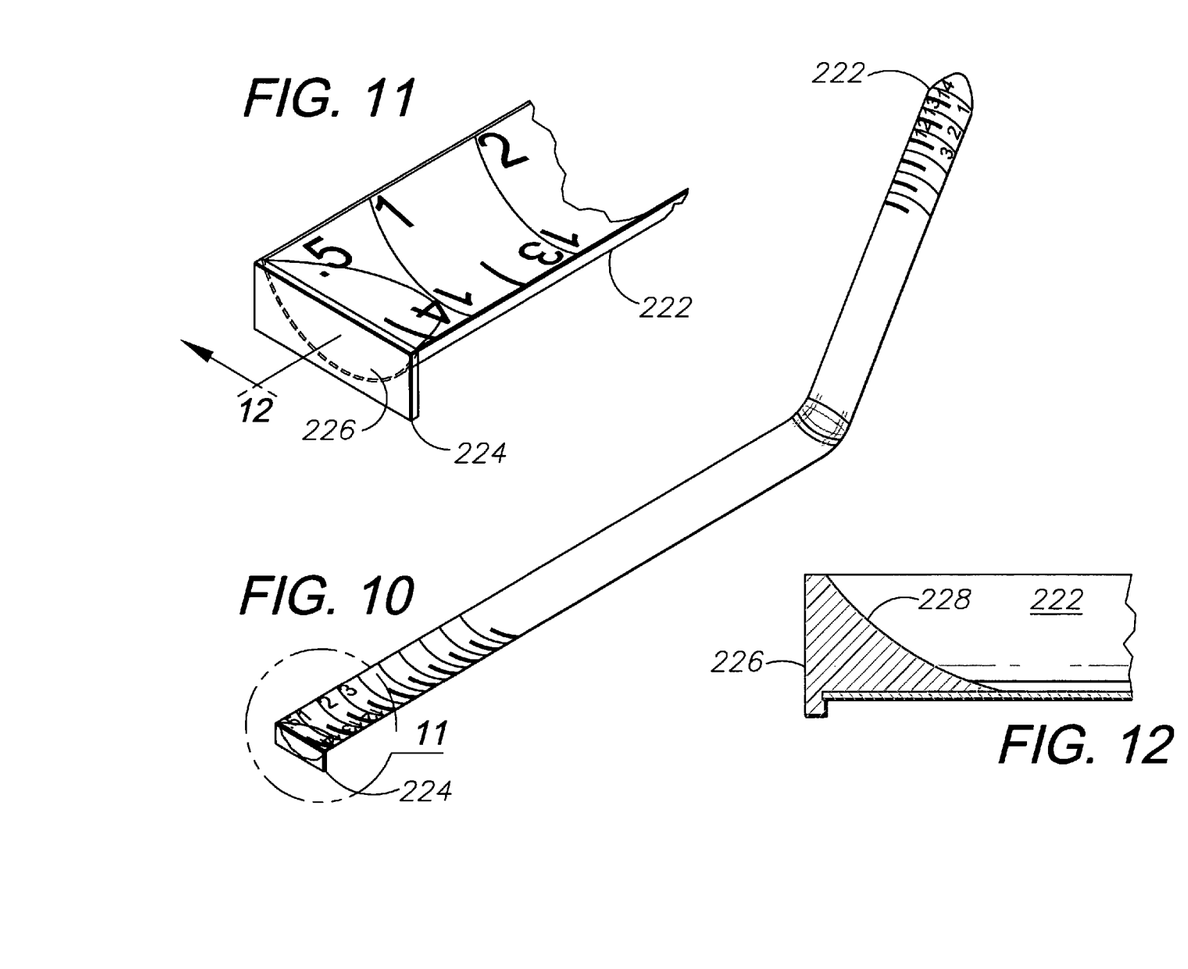
FIG. 10 is a perspective view of a subsurface wound measuring device comprising another alternative embodiment of the present invention.
FIG. 11 is a fragmentary, perspective view thereof, taken generally within circle 11 in FIG. 10.
FIG. 12 is a fragmentary, longitudinal cross-sectional view thereof, taken generally along line 12-12 in FIG. 11.

FIGS. 10-12 show an alternative embodiment measuring strip 222, which includes a flat or blunt first end structure 224, which is adapted for abutting a wound cavity surface. The blunt-ended configuration of the end structure 224, which presents a relatively flat engagement face 226, reduces or eliminates penetration into tissue within wound cavities, whereby relatively accurate length measurements can be taken with minimal patient discomfort. The end structure 224 includes a fillet 228, which flares into the upper surface of the measuring strip 222.

Figure 13:
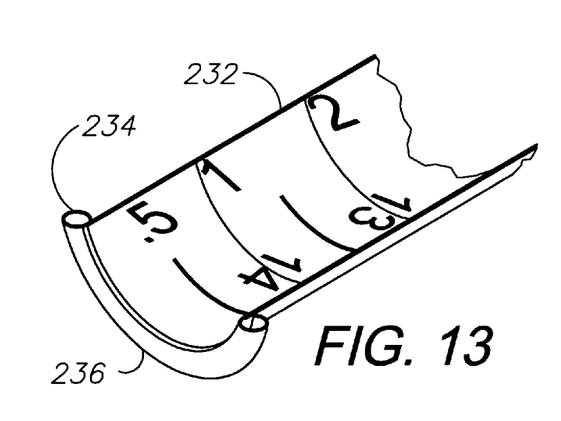
FIG. 13 is a fragmentary, perspective view of a subsurface wound measuring device comprising another alternative embodiment of the present invention.
Figure 13A:
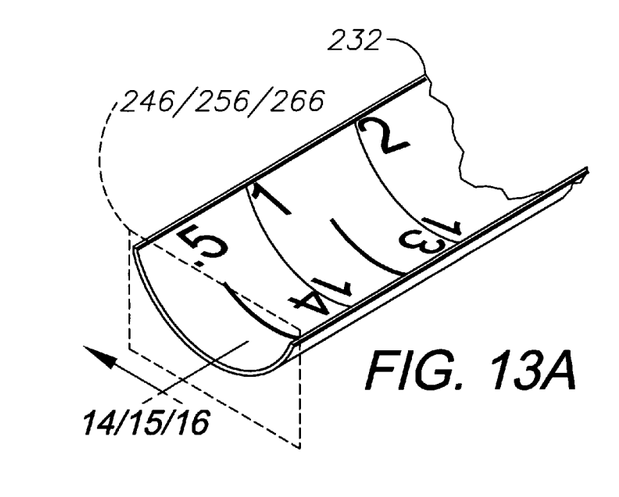
FIG. 13A is a fragmentary, perspective view of a subsurface wound measuring device, which can be fitted with various end configurations, as shown in cross-sectional FIGS. 14-16 taken generally along line 14/15/16 in FIG. 13A.
Figure 14:
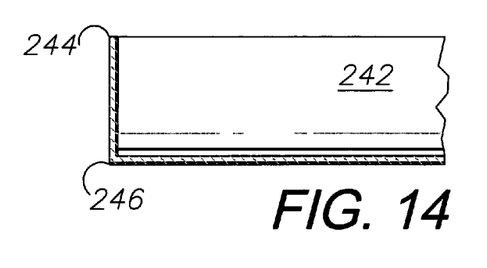
Figure 15:
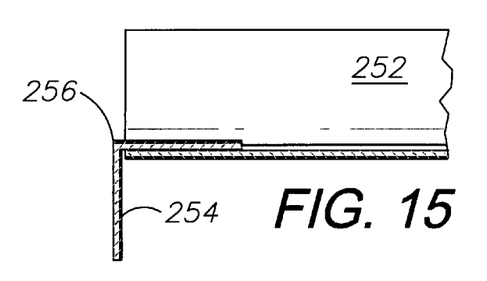
Figure 16:
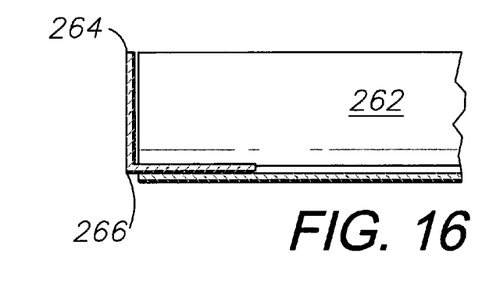

FIG. 13 shows another alternative embodiment measuring strip 232, which includes an arcuate, upwardly-concave lip 234 forming a first end structure 236 with a generally tubular configuration adapted for minimizing patient discomfort and providing accurate readings. FIGS. 14-16 comprise fragmentary, cross-sectional views taken generally along line 14/15/16 in FIG. 13A, which shows a portion of alternative embodiment measuring strips 242, 252 and 262 and the general location of end structures 246, 256 and 266 in relation thereto. FIGS. 14-16 show the further alternative embodiment measuring strips 242, 252 and 262 respectively with the end structures 246, 256 and 266 including flanges 244, 254 and 264. The end structure 246 is integrally formed with the measuring strip 242. The end structures 256, 266 comprise separate clips attached to the measuring strips 252, 262 with the flanges 254, 264 depending downwardly and extending upwardly therefrom respectively.

Figure 17:
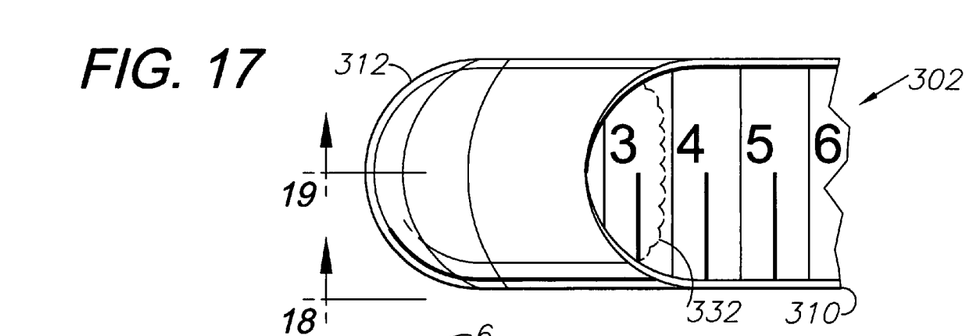
FIG. 17 is a fragmentary, top plan view of another alternative wound measuring device, which is adapted for retrieving tissue and fluid samples.
Figure 18:
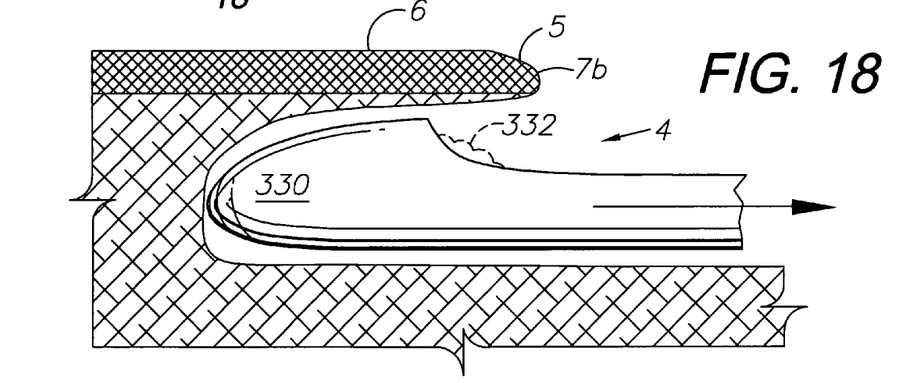
FIG. 18 is a fragmentary, side elevational view thereof, shown in a tissue or fluid sample gathering position within a wound, taken generally along line 18 in FIG. 17.
Figure 19:
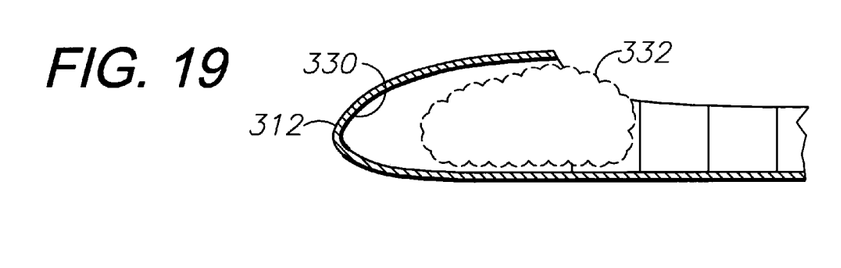
FIG. 19 is a fragmentary, cross-sectional view thereof, taken generally along line 19 in FIG. 17.

FIGS. 17-19 show another alternative embodiment biopsy/measuring device 302 comprising a measuring strip 310 with a first end 312 forming a distally-opened receptacle 330 adapted for receiving and extracting a tissue or fluid sample 332, e.g. for culture purposes in connection with a biopsy. The device 302 can be used for sample collecting, measuring or both in one or more procedures. For example, in connection with measuring an undermined wound cavity, samples can be collected for analysis whereby treatment progress and potential pathogenic conditions can be monitored by analyzing the collected samples.

It will be appreciated that various other end structures can be provided for the guide and measuring strips, including disposable tips and absorbable materials for applying pharmaceuticals or taking fluid samples. Moreover, the guide and measuring strip end structures can be modified by medical practitioners as necessary to accommodate a wide range of wound cavities among patients having unique conditions and treatment procedures.

It is to be understood that the invention can be embodied in various forms, and is not to be limited to the examples discussed above. Other components and configurations can be utilized in the practice of the present invention.

Having thus described the invention, what is claimed as new and desired to be secured by Letters Patent is:

1. A wound measuring method for measuring at least one physical parameter of a patient with a subsurface wound having a cavity with a cavity opening and a sidewall, said method comprising:
    providing a measuring device with a flexible measuring strip having a first end, a second end and an exterior surface with measuring indicia;
    providing said measuring device with a flexible guide strip having a first end, a second end and an exterior surface;
    providing each said strip with a generally arcuate, concave, transverse, cross-sectional configuration;
    providing a collar or sleeve with a passage extending therethrough;
    slidably receiving said measuring strip in said collar or sleeve passage in a frictional, gripping relation;
    inserting the flexible guide strip at least partially into the cavity by the flexible guide strip second end, the second end extending towards the cavity opening, the first end extending towards the cavity sidewall;
    inserting the flexible measuring strip at least partially into the cavity in sliding contact on the guide strip with the measuring strip first end extending towards the cavity sidewall;
    locating the measuring device in association with the cavity sidewall;
    identifying a distance along the cavity sidewall with the measuring indicia;
    forming a bend in the flexible measuring strip at a variably repositionable bend location between said measuring strip first and second ends;
    relating the bend location to a dimension of the cavity;
    dividing said flexible measuring strip at said bend into first and second semi-rigid sections terminating at said first and second strip ends respectively;
    moving the collar or sleeve into position in proximity said bend to maintain the bend and to provide a visual reference for the bend location along the flexible measuring strip, and further to lock the position of the flexible measuring strip in place;
    identifying the distance with said first and second semi-rigid sections extending along respective portions of said cavity;
    recording the distance;
    providing a receptacle with a closed end at the measuring strip first end;
    providing the receptacle with an opening in spaced relation and oriented away from said measuring strip first end;
    obtaining a tissue or fluid sample in said receptacle from within said wound; and
    extracting said sample from the wound and analyzing said sample.

2. The wound measuring method according to claim 1, which includes the additional step of providing said receptacle with a radiused configuration.

\* \* \* \* \*